United States Patent [19]
Perri et al.

[11] Patent Number: 5,663,422
[45] Date of Patent: Sep. 2, 1997

[54] PROCESS FOR THE PRODUCTION OF 1,2-DIACETOXY ESTERS

[75] Inventors: Steven Thomas Perri; Stephen Neal Falling, both of Kingsport, Tenn.

[73] Assignee: Eastman Chemical Company, Kingsport, Tenn.

[21] Appl. No.: 609,698

[22] Filed: Mar. 1, 1996

[51] Int. Cl.$^6$ .................................................. C07C 69/28
[52] U.S. Cl. .................................................. 560/240
[58] Field of Search .............................................. 560/240

[56] References Cited

U.S. PATENT DOCUMENTS 5,189,199  2/1993  Godleski .................................. 560/93

OTHER PUBLICATIONS

Paust, J., *Pure and Appl. Chem.*, 63, p. 45 (1991).
Shvets, V. F., et al., *Kinet. Katal.*, 16(3), pp. 785–788 (1975).
Shvets, V. F., et al., *Kinet. Katal.*, 16(2), pp. 425–430 (1975).
Swindell, C. S., et al., *J. Org. Chem.*, 55, p. 3 (1990).
Fraser–Reid, B., et al., *J. Amer. Chem. Soc.*, 107, p. 5576 (1985).
Evans, R. M., et al., *J. Chem Soc.*, p. 248 (1949).
Ali, S., et al., *J. Org. Chem.*, 53, p. 5547, (1988).

*Primary Examiner*—Nicky Chan
*Attorney, Agent, or Firm*—Cheryl J. Tubach; Harry J. Gwinnell

[57] ABSTRACT

A process for the preparation of a 1,2-diacetoxy ester comprises acetylation of an epoxide with an acetic anhydride in the presence of a quaternary phosphonium acetate catalyst or its complex with acetic acid.

15 Claims, 4 Drawing Sheets

PROCESS FOR THE PRODUCTION OF 1,2-DIACETOXY ESTERS

TECHNICAL FIELD

This invention relates to processes for acetylation of epoxides with acetic anhydride to produce 1,2-diacetoxy esters. More particularly, this invention relates to catalysts for such processes.

BACKGROUND OF THE INVENTION 1,2-Bis(acyloxyates) are useful intermediates for organic synthesis. For example, 3,4-diacetoxy-1-butene is used in the production of vitamin A acetate, Paust, J., *Pure and Appl. Chem.*, 63, 45 (1991). The 1,2-bis(acyloxyates) are the bis-esters of 1,2-dihydroxy compounds, or, alternatively, 1,2-diol dicarboxylates. Of particular interest is the 1,2-diacetoxy esters having the general formula as shown in structure (I).

In the preparation of 1,2-diacetoxy esters by acetylation of epoxides with acetic anhydride various forms or combinations of amine catalysts have been used. For example, a study by Shvets and Al-Wahib discloses that 1,2-diacetoxyethane can be prepared from ethylene oxide with acetic anhydride in the presence of pyridine and that the reaction proceeds by the intermediacy of N-(β-acetoxyethyl) pyridinium acetate. The reaction produces yields ranging from 45 to 93.5 percent. The yields decrease with increasing pyridine concentration at 0.05 to 1.00M. Shvets, V. F. and Al-Wahib, I., *Kinet. Katal.*, 16(3), 785–8 (1975).

In another study by Shvets and Al-Wahib the nucleophilic catalysis of ethylene oxide is disclosed. The reaction of ethylene oxide with acetic anhydride is catalyzed by $(CH_3CH_2)_4N^+X^-$ (X=Cl, Br, I) and proceeds by attack of the halide anion on ethylene oxide to form the 2-haloethyl acetate and $(CH_3CH_2)_4N^+OAc^-$. The latter product continues to catalyze the reaction of ethylene oxide with acetic anhydride and also reacts with the 2-haloethyl acetate so that both processes lead to 1,2-diacetoxyethane. Product yields are typically low when using tetraalkylammonium halides. Shvets, V. F. and Al-Wahib, I., *Kinet. Katal.*, 16(2), 425–30 (1975).

As taught by Swindell, the nucleophilic catalysis of an epoxycyclooctane derivative with acetic anhydride catalyzed by 1,8-diazabicyclo [5.4.0]undec-7-ene (DBU) and LiCl in tetrahydrofuran produces the corresponding 1,2-diacetoxy ester at a 70 percent yield, Swindell, C. S. and Patel, B. P., *J. Org. Chem.*, 55, 3 (1990). Fraser-Reid discloses that the reaction of epoxy-pyranosides with acetic anhydride catalyzed by $(CH_3CH_2CH_2CH_2)_4N^+OAc^-$ opens the epoxy ring to prepare the corresponding 1,2-diacetoxy ester, Fraser-Reid, B. and Rahman, Md. A., *J. Amer. Chem. Soc.*, 107, 5576 (1985).

Tetraalkylammonium acetates are produced by alkylation of a tertiary amine to form a quaternary ammonium salt in which the counterion is exchanged for acetate. Generally, this process requires isolation or purification of the intermediates. Further, the tetraalkylammonium acetates are not thermally stable. For example, tetrabutylammonium acetate rapidly decomposes upon heating over a range of 25°–400° C. At 165° C., tetrabutylammonium acetate retains 90% of its mass, at 190° C. 50% of its mass and at 230° C. 8% of its mass. The thermal instability of tetraalkylammonium acetates decreases catalyst lifetime and hinders the ability to easily recycle the catalyst.

The acid catalyzed ring opening of epoxides in the presence of acetic anhydride is also well known. For example, the acetylation of 3,4-epoxy-1-butene in the presence of acetic anhydride produces 3,4-diacetoxy-1-butene as disclosed by Evans, R. M., Fraser, J. B. and Owen, L. N., *J. Chem Soc.*, 248 (1949). A 70 percent yield is obtained when using hydrochloric acid as the catalyst, while only a 39 percent yield is obtained using anhydrous zinc chloride as the catalyst. Another example of a Lewis acid catalyzed ring opening of an epoxide is disclosed by Ali, S. and Bittman, R., *J. Org. Chem.*, 53, 5547, (1988) which describes the diacylation of glycidyl tosylate in the presence of boron trifluoride etherate with a 76 percent yield. These Lewis acid catalyzed acylations give reasonable yields. However, in practice Lewis acid catalysts do not give good process economics on large scale due to catalyst costs and the need to use expensive, corrosion-resistant materials of construction.

U.S. Pat. No. 5,189,199 to Godleski discloses the addition of oxygen nucleophiles to 3,4-epoxy-1-butene catalyzed by ligated Pd(0) to prepare 1,4-disubstituted-2-butenes. However, applying this process for the production of 3,4-diacetoxy-1-butene using acetic anhydride requires additional separation because it predominately produces 1,4-diacetoxy-2-butene. Its application is limited in scope since the substrate must be an epoxide in direct conjugation with a carbon—carbon double bond.

Other processes are commonly used to prepare 1,2-diacetoxy esters such as the acetylation of 1,2-diols with acetic anhydride or acetyl chloride. However, when using acetic anhydride, acetic acid is co-produced and must be removed or recycled in the process. With acetyl chloride, an excess of an organic base is generally needed to remove the corrosive hydrochloric acid that is co-produced in the process. A large scale process utilizing acetyl chloride is inefficient since the hydrochloride salt needs to be treated to either regenerate the base or dispose of in a waste stream. In most cases, 1,2-diacetoxy esters are prepared from epoxides by acid catalyzed hydrolysis of epoxides to form the corresponding 1,2-dihydroxy derivative followed by acetylation of the hydroxyl groups with an equivalent amount of acetic anhydride and organic base, such as pyridine or 4-(N,N-dimethylamino)pyridine. This overall process requires two chemical steps and isolation of intermediates.

Thus, there exists a need whereby 1,2-diacetoxy esters may be produced from epoxides in a single step without the need to use corrosion resistant equipment, without the added costs of separating co-products and recovering by-products of the process and without the waste associated with the loss of catalysts due to thermal instability. Accordingly, it is to the provision of such improved processes for the preparation of 1,2-diacetoxy esters that the present invention is primarily directed.

SUMMARY OF THE INVENTION

A process for the preparation of a 1,2-diacetoxy ester comprises acetylation of an epoxide with acetic anhydride in the presence of a quaternary phosphonium acetate catalyst or its complex with acetic acid.

DETAILED DESCRIPTION OF THE INVENTION

In the preparation of 1,2-diacetoxy esters by the catalytic acetylation of epoxides with acetic anhydride, the use of quaternary phosphonium acetate catalysts or their complexes with acetic acid has now been discovered to provide an improved process which has increased thermal stability in the catalyst allowing for reuse of the catalyst and which may be conducted in a one step process with the consumption of both acetyl functions resulting in no co-product formation.

In the conversion of the epoxides to the 1,2-diacetoxy esters, the epoxide rings are believed to be cleaved with acetate anion with concomitant acetylation of the incipient alkoxide thereby producing 1,2-diacetate esters. The 1,2-diacetoxy esters produced in accordance with the present invention have the structure:

(I)

wherein the R substituents are defined below with respect to the epoxide.

The epoxide reactants contain from 2 to about 20 carbon atoms, preferably from 3 to 8 carbon atoms. Examples of the epoxide reactants include compounds having the structural formula:

(II)

wherein each R substituent is independently selected from hydrogen, alkyl or alkenyl of up to about 8 carbon atoms, carbocyclic, aryl or heterocyclic aryl of about 5 to 10 carbon atoms or any two R substituents collectively may represent an alkyl or alkenyl forming a ring, e.g., alkyl containing in the main chain 3 to about 6 carbon atoms. The preferred epoxide reactants comprise compounds of formula (II) wherein the R substituents individually represent hydrogen or a straight or branched chain alkyl or alkenyl of 2 to about 8 carbon atoms, especially compounds of formula (II) wherein 2 or more of the R substituents represent hydrogen.

Exemplary compounds contemplated for use in the practice of the present invention include 1,2-butylene oxide, 2,3-epoxybutane, 3,4-epoxy-1-butene, ethylene oxide, propylene oxide, styrene oxide, cyclohexene oxide, and the like. The epoxide reactant of primary interest is 3,4-epoxy-1-butene.

The quaternary phosphonium acetate catalysts have the formula (III) and are commercially available as complexes with acetic acid (IV):

(III)

(IV)

wherein Ac represents the acetyl group n is less than or equal to 1 and each R' substituent is independently selected from an alkyl, alkenyl or aromatic group of 1 to 8 carbon atoms. The alkyl groups may be linear chains or cyclic groups. Exemplary compounds contemplated include tetrabutylphosphonium acetate, ethyltriphenylphosphonium acetate, tetraoctylphosphonium acetate and the like.

The significance of the invention is demonstrated in the conjugated epoxyalkene system of 3,4-epoxy-1-butene by the regioselective addition process of acetic anhydride in the presence of a tetrabutylphosphonium acetate to prepare 3,4-diacetoxy-1-butene, a key intermediate in the manufacture of Vitamin A Acetate. Such acetylations of 3,4-epoxy-1-butene conducted under moderate temperatures of 80° to 160° C. at atmospheric pressure or under moderate pressure of an inert gas, such as nitrogen, give distilled yields of 80–88% 3,4-diacetoxy-1-butene with no 1,4-diacetoxy-2-butene.

As compared to the prior art, the use of the quaternary phosphonium acetate catalysts of this invention provides advantages over the use of tetra-alkylammonium acetates in that the quaternary phosphonium acetates are generally stable, solid catalysts and are thermally more stable than most tetraalkylammonium acetates. For example, tetrabutylammonium acetate rapidly decomposes upon heating over a range of 25°–400° C. At 165° C. tetrabutylammonium acetate retains 90% of its mass, at 190° C. it retains 50% of its mass and at 230° C. it retains 8% of its mass. Whereas, tetrabutylphosphonium acetate slowly decomposes upon heating over a range of 25°–400° C. At 209° C. tetrabutylphosphonium acetate retains 90% of its mass, at 342° C. it retains 50% of its mass and at 375° C. it retains 10% of its mass. The thermal stability of quaternary phosphonium acetates, therefore, offer longer catalyst lifetime with the ability to easily recycle the catalyst by distilling the product away from the non-volatile catalyst. The recovered quaternary phosphonium acetate may then be reused by the addition of more substrate and acetic anhydride to carry out the reaction in a batchwise process or continuous process.

Tetrabutylphosphonium acetate catalyst may be recycled such as in a batch reaction of acetic anhydride and 3,4- epoxy-1-butene. The desired 3,4-diacetoxy-1-butene is obtained by distillation of 3,4-diacetoxy-1-butene from the reaction mixture and by resubjecting the distillation residue to a new charge of acetic anhydride and 3,4-epoxy-1-butene to repeat the process.

The acetylation conditions of temperature and pressure may vary depending on the reactants and catalysts employed. The acylation is generally conducted from about 60° to 175° C. The preferred temperature of operation is in the range of 100° to 150° C. The process may be carried out under atmospheric pressure to about 250 psig (35.5 bar). The use of moderate pressures of about 50 to 250 psig (4.6 to 35.5 bar) are advantageous when low boiling reactants are employed. As noted above, the optimum combination of temperature and pressure depends on other process variables but can be readily ascertained by those skilled in the art.

The process of this invention optionally may be carried out in the presence of an inert, organic solvent. Examples of such solvents include aliphatic and aromatic hydrocarbons such as cyclohexane, heptane, toluene, p-xylene and mixed xylene isomers, ethers such as tetrahydrofuran, and amides such as N,N-dimethyl-formamide and N-methyl-2-pyrrolidone. The preferred solvent system is the acetic anhydride which is used both as a solvent and reactant. The acetic anhydride is generally present in amounts of 1.0 molar equivalent to a large molar excess of acetic anhydride relative to epoxide.

The process may be carried out in a batch, semi-continuous or continuous mode of operation. For example, batch operation may comprise agitating acetic anhydride, tetraalkylphosphonium acetate and 3,4-epoxy-1-butene in a vessel for a time sufficient to acylate essentially all of the 3,4-epoxy-1-butene to 3,4-diacetoxy-1-butene. The tetraalkylphosphonium acetate catalyst may be separated from the acylated mixture by fractional distillation of the reaction mixture. That is, after removing low boilers, the 3,4-diacetoxy-1-butene is distilled overhead and the non-volatile tetraalkylphosphonium acetate catalyst remains in the base.

The process provided by the present invention is further illustrated by the following examples which are intended to be exemplary of the invention.

Gas chromatographic (GC) analyses were performed on a Hewlett-Packard 5890A gas chromatograph with a 30 meter, DB-5, 0.32 mm inside-diameter, capillary column with a 1.2 micron film thickness. Diglyme was used as an internal standard to reference composition percentages for kinetic experiments (Examples 8–13). The temperature program was 35° C. at 4.5 minutes, 20° C. increase per minute to 240° C. and hold 20 minutes. The identities of the products obtained were confirmed by nuclear magnetic spectrometry and gas chromatography-mass spectrometry. $^1$H NMR were recorded on a Gemini 300 MHz spectrometer and $^{13}$C NMR were recorded at 75 MHz.

Thermogravimetric analyses were conducted on a General V4.1C Dupont 200. Reagent grade acetic anhydride was used without further purification. Tetrabutylphosphonium acetate and ethyltriphenylphosphonium acetate were supplied by Johnson Matthey, Inc. of Ward Hill, Mass. as a complex with acetic acid in a 70 weight percent (wt %) solution in methanol. The catalysts were prepared by removal of the methanol by concentration at reduced pressure on a rotary evaporator at 80°–90° C. The quaternary phosphonium acetate catalysts were then stored under argon. Tetraoctylphosphonium acetate was prepared by anion exchange of tetraoctylphosphonium iodide with silver acetate then treated with an equivalent of acetic acid to make the acetic acid complex.

EXAMPLE 1

A 300-mL, 3-necked flask fitted with a thermocouple, condenser and stopper was charged with 90.5 mL (0.88 mol) acetic anhydride, 62.7 mL (0.80 mol) 3,4-epoxy-1-butene and 12.1 g (0.032 mol) of tetrabutylphosphonium acetate acetic acid complex (Bu$_4$POAc.HOAc). The flask was purged with nitrogen then heated to reflux. The reaction was discontinued after 4 hrs during which time the temperature increased to 150° C. GC analysis revealed complete conversion of the 3,4-epoxy-1-butene to the desired 3,4-diacetoxy-1-butene. The reaction mixture was distilled at 4.5 Torr. Three fractions were obtained with the last fraction containing the pure 3,4-diacetoxy-1-butene with a mass of 121.5 g and a yield of 88% (Table 1 and 2). Fraction 1: 17.5 g, bp 40°–80° C. (76% acetic anhydride, 19% 3,4-diacetoxy-1-butene); Fraction 2: 4.2 g, bp 80°–92° C. (89% 3,4-diacetoxy-1-butene); Fraction 3: 121.5 g, bp 92°–95° C. (99.6% 3,4-diacetoxy-1-butene). Spectral data for Fraction 3 was as follows: $^1$H NMR (CDCl$_3$) δ 5.78 (m, 1 H), 5.46 (m, 1 H), 5.33 (dd, J=1.1, 17.3 Hz, 1 H), 5.25 (dd, J=1.1, 10.3 Hz, 1 H), 4.22 (dd, J=3.7, 12.0 Hz, 1 H), 4.07 (dd, J=7.1, 12.0 Hz, 1 H), 2.07 (s, 3 H), 2.04 (s, 3 H); $^{13}$C NMR (CDCl$_3$) δ 170.4, 169.7, 132.1, 118.5, 71.8, 64.5, 20.8, 20.5.

EXAMPLE 2

A 300-mL, 3-necked flask fitted with a thermocouple, condenser and stopper was charged with 90.5 mL (0.88 mol) acetic anhydride, 31.0 g (0.44 mol) 3,4-epoxy-1-butene and 3.5 g (0.005 mol) of ethyltriphenylphosphonium acetate acetic acid complex (Et(C$_6$H$_5$)$_3$POAc.HOAc). The flask was purged with nitrogen then heated to reflux. The reaction was discontinued after 4 hrs during which time the temperature increased to 156° C. GC analysis revealed complete conversion of the 3,4-epoxy-1-butene to the desired 3,4-diacetoxy-1-butene. The reaction mixture was distilled at 10–3.5 Torr. Three fractions were obtained with the last fraction containing the pure 3,4-diacetoxy-1-butene with a mass of 64.9 g and a yield of 88% (Table 1). Fraction 1: 50.3 g, bp 40°–45° C. at 20–6 Torr (98% acetic anhydride); Fraction 2: 3.0 g, bp 45°–78° C. at 3.5 Torr (60.2% 3,4-diacetoxy-1-butene); Fraction 3: 64.9 g, bp 78°–80° C. at 3.5 Torr (99.9% 3,4-diacetoxy-1-butene). This example demonstrates the use of a different quaternary phosphonium catalyst.

EXAMPLE 3

A 300-mL, 3-necked flask fitted with a thermocouple, condenser and stopper was charged with 90.5 mL (0.88 mol) acetic anhydride, 31.0 g (0.44 mol) 3,4-epoxy-1-butene and 1.75 g (0.003 mol) of tetraoctylphosphonium acetate acetic acid complex ((C$_8$H$_{17}$)$_4$POAc.HOAc). The flask was purged with nitrogen then heated to reflux. The reaction was discontinued after 12 hrs during which time the temperature increased to 148° C. GC analysis revealed complete conversion of the 3,4-epoxy-1-butene to the desired 3,4-diacetoxy-1-butane. The reaction mixture was distilled at 20–3.5 Torr. Three fractions were obtained with the last fraction containing the pure 3,4-diacetoxy-1-butene with a mass of 63.8 g and a yield of 84% (Table 1). Fraction 1: 52.4 g, bp 50°–75° C. at 20–3.5 Torr (88% acetic anhydride); Fraction 2: 1.1 g, bp 75°–78° C. at 3.5 Torr (68% 3,4-diacetoxy-1-butene); Fraction 3: 63.8 g, bp 78°–80° C. at 3.5 Torr (99.4% 3,4-diacetoxy-1-butene). This example demonstrates the use of a different quaternary phosphonium catalyst.

TABLE 1

| Example | Rxn Time (Hrs.) | Catalyst | Catalyst (mol) | 3,4-Epoxy-1-butene (mol) | $Ac_2O$ (mol) | % Isolated 3,4-Diacetoxy-1-Butene |
|---|---|---|---|---|---|---|
| 1 | 4 | $Bu_4POAc.HOAc$ | 0.032 | 0.80 | 0.88 | 88 |
| 2 | 4 | $Et(C_6H_5)_3POAc.HOAc$ | 0.005 | 0.44 | 0.88 | 88 |
| 3 | 12 | $(C_8H_{17})_4POAc.HOAc$ | 0.003 | 0.44 | 0.88 | 84 |

EXAMPLE 4

A 300-mL, 3-necked flask fitted with a thermocouple, condenser and stopper was charged with 90.5 mL (0.88 mol) acetic anhydride, 56.7 mL (0.80 mol) propylene oxide and 7.6 g (0.02 mol) of tetrabutylphosphonium acetate acetic acid complex. The flask was purged with nitrogen then heated to reflux. The reaction was discontinued after 22 hrs during which time the temperature increased to 160° C. GC analysis revealed complete conversion of the propylene oxide to the desired 1,2-diacetoxy-propane. The reaction mixture was distilled at 4 Torr. Four fractions were obtained with the last three fractions containing the pure 1,2-diacetoxypropane with a combined mass of 114 g and a yield of 89% (Table 2). Fraction 1: 8 g, bp 35°–70° C. (98% acetic anhydride); Fraction 2: 6.3 g, bp 70°–72° C. (98% 1,2-diacetoxy-propane); Fraction 3: 11 g, bp 72°—72° C. (99% 1,2-diacetoxypropane); Fraction 4: 11 g, bp 72°–74° C. (100% 1,2-diacetoxypropane). Spectral data for Fraction 4 was as follows: $^1$H NMR ($CDCl_3$) δ 5.04 (m, 1 H), 4.09 (dd, J=6.6, 11.8 Hz, 1 H), 2.00 (s, 3 H), 1.98 (s, 3 H), 1.17(d, J=6.5 Hz, 3 H); $^{13}$C NMR ($CDCl_3$) δ 170.6, 170.3, 68.1, 65.9, 21.0, 20.6, 16.3.

EXAMPLE 5

A 300-mL, 3-necked flask fitted with a thermocouple, condenser and stopper was charged with 71.4 g (0.70 mol) acetic anhydride, 25.0 g (0.35 mol) 1,2-butylene oxide and 3.4 g (0.009 mol) of tetrabutylphosphonium acetate acetic acid complex. The flask was purged with nitrogen then heated to reflux. The reaction was discontinued after 14 hrs during which time the temperature increased to 153° C. GC analysis revealed complete conversion of the 1,2-butylene oxide to the desired 1,2-diacetoxybutane. The reaction mixture was distilled at 10–3 Torr. Four fractions were obtained with the last two fractions containing the pure 1,2-diacetoxybutane with a combined mass of 53.8 g and a yield of 88% (Table 2). Fraction 1: 36 g, bp 45°–65° C. at 10 Torr (98% acetic anhydride); Fraction 2: 3.6 g, bp 65°–70° C. at 3 Torr (91% 1,2-diacetoxybutane); Fraction 3: 38 g, bp 70°–72° C. at 3 Torr (100% 1,2-diacetoxybutane); Fraction 4: 15.8 g, bp 72°–74° C. (99.4% 1,2-diacetoxybutane). Spectral data for Fraction 4 was as follows: $^1$H NMR ($CDCl_3$) δ 4.95 (m, 1 H), 4.18 (dd, J=3.4, 11.9 Hz, 1 H), 3.98 (dd, J=6.6, 11.9 Hz, 1 H), 2.00 (s, 3 H), 1.99 (s, 3 H), 1.55 (q, J=7.5 Hz, 2 H), 0.88 (t, J=7.5 Hz, 3 H); $^{13}$C NMR ($CDCl_3$) δ 170.6, 170.4, 72.6, 64.6, 23.6, 20.8, 20.6, 9.3. This example shows the acetylation of a different epoxide.

EXAMPLE 6

A 300-mL, 3-necked flask fitted with a thermocouple, condenser and stopper was charged with 49 mL (0.48 mol) acetic anhydride, 28.3 g (0.24 mol) styrene oxide and 3.8 g (0.010 mol) of tetrabutylphosphonium acetate acetic acid complex. The flask was purged with nitrogen then heated to reflux. The reaction was discontinued after 1.5 hrs during which time the temperature increased to 162°–C. GC analysis revealed complete conversion of the styrene oxide to the desired 1,2-diacetoxy-1-phenylethane. The reaction mixture was distilled at 10–0.6 Torr. Three fractions were obtained with the last fraction containing the pure 1,2-diacetoxy-1-phenylethane with a total mass of 48.1, g and a yield of 90% (Table 2). Fraction 1: 26.5 g, bp 35°–40° C. at 10 Torr (98% acetic anhydride); Fraction 2: 1.1 g, bp 110°–114° C. at 0.6 Torr (87% 1,2-diacetoxy-1-phenylethane); Fraction 3: 48.1 g, bp 99°–100° C. at 0.15 Torr (99.6% 1,2-diacetoxy-1-phenylethane). Spectral data for Fraction 3 was as follows: $^1$H NMR ($CDCl_3$) δ 7.34 (m, 5 H), 6.03 (dd, J=3.5, 7.7 Hz, 1 H), 4.33 (m, 2 H), 2.12 (s, 3 H), 2.06 (s, 3 H); $^{13}$C NMR ($CDCl_3$) δ 170.5, 169.9, 136.4, 128.6, 128.5, 126.6, 73.2, 66.0, 21.0, 20.7. This example shows the acetylation of a different epoxide.

EXAMPLE 7

A 300-mL, 3-necked flask fitted with a thermocouple, condenser and stopper was charged with 50 mL (0.53 mol) acetic anhydride, 26.0 g (0.265 mol) cyclohexene oxide and 4.0 g (0.011 mol) of tetrabutylphosphonium acetate acetic acid complex. The flask was purged with nitrogen then heated to reflux. The reaction was discontinued after 2 hrs during which time the temperature increased to 153° C. GC analysis revealed complete conversion of the cyclohexene oxide to the desired trans-1,2-diacetoxycyclohexane. The reaction mixture was distilled at 10–0.45 Torr. Three fractions were obtained with the last fraction containing the pure 1,2-diacetoxycyclohexane with a total mass of 41.4 g and a yield of 78% (Table 2). Fraction 1: 22.4 g, bp 65°–70° C. at 10 Torr (98% acetic anhydride); Fraction 2: 6 g, bp 68°–71° C. at 0.5 Torr (78% 1,2-diacetoxycyclohexane); Fraction 3: 41.4 g, bp 72°–76° C. at 0.45 Torr (99.3% 1,2-diacetoxycyclohexane). Spectral data for Fraction 3 was as follows: $^1$H NMR ($CDCl_3$) δ 4.75 (m, 2 H), 2.01 (m, 2 H), 1.98 (s, 6 H), 1.69 (m, 2 H), 1.32 (brm, 4 H); $^{13}$C NMR ($CDCl_3$) δ 170.3, 73.6, 30.0, 23.3, 21.0. This example shows the acetylation of a different epoxide.

TABLE 2

| Example | Rxn Time (Hrs.) | Epoxide | Moles of Epoxide | Moles of Ac$_2$O | Moles of Bu$_4$POAc.HOAc | % Isolated 1,2-Diacetate |
|---|---|---|---|---|---|---|
| 1 | 4 | 3,4-Epoxy-1-Butene | 0.80 | 0.88 | 0.032 | 88 |
| 4 | 22 | Propylene Oxide | 0.80 | 0.88 | 0.020 | 89 |
| 5 | 14 | 1,2-Butylene Oxide | 0.35 | 0.70 | 0.009 | 88 |
| 6 | 1.5 | Styrene Oxide | 0.24 | 0.48 | 0.010 | 90 |
| 7 | 2 | Cyclohexene Oxide | 0.265 | 0.53 | 0.011 | 78 |

Kinetic Affect of Quaternary Phosphonium Catalyst

Figure 1:
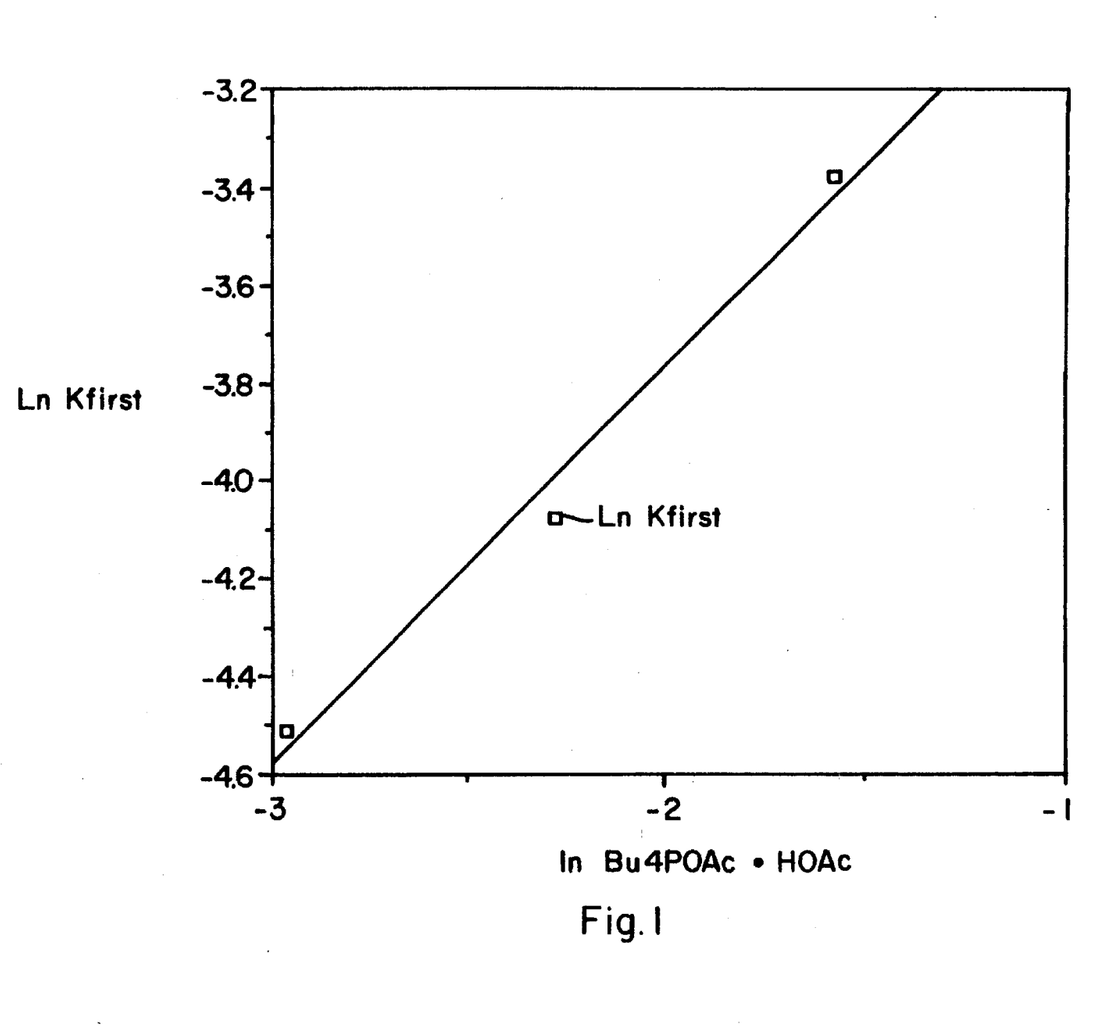
FIG. 1 is a graph demonstrating the dependence of tetrabutylphosphonium acetate concentration in the acetylation of 3,4-epoxy-1-butene with acetic anhydride by the correlation of the natural logarithm (ln) of the first order rate constant versus ln of the tetrabutyl-phosphonium acetate concentration.

The affect of tetrabutylphosphonium acetate catalyst on the rate of addition of acetic anhydride to 3,4-epoxy-1-butene to form 3,4-diacetoxy-1-butene is demonstrated in Examples 8–10 (Table 3). In all of the studies conducted, the dependence of 3,4-epoxy-1-butene concentration was observed to be first order. The dependence of the tetrabutylphosphonium acetate concentration under conditions giving the most favorable process economics resulted in acetic anhydride concentrations in slight excess of the 3,4-epoxy-1-butene concentration (Examples 8–10, Table 3). The dependence of tetrabutylphosphonium acetate concentration is correlated with the rate constant by plotting the ln of the first order rate constant versus ln of the tetrabutylphosphonium acetate concentration in FIG. 1. The dependence on tetrabutylphosphonium acetate concentration is expressed as the slope (0.82) of the ln of the first order rate constant versus ln of the tetrabutylphosphonium acetate concentration and indicates a dependance that is less than first order. This reaction order suggests that the tetrabutylphosphonium acetate catalyst acts in a complex mechanism and may be involved in more than one step of the mechanism besides the rate determining step. A linear correlation of 0.984 indicates a very good correlation in the range of 0.05–0.2M tetrabutylphosphonium acetate concentration.

TABLE 3

| Example | (min-1) | Bu$_4$POAc.HOAc M | 3,4-Epoxy-1-Butene | ln Kfirst | ln Bu$_4$POAc.HOAc M |
|---|---|---|---|---|---|
| 8 | 0.011 | 0.052 | 5.21 | −4.51 | −2.957 |
| 9 | 0.017 | 0.103 | 5.21 | −4.075 | −2.273 |
| 10 | 0.034 | 0.206 | 5.21 | −3.381 | −1.579 |

EXAMPLE 8

A 100-mL autoclave was charged with 45.25 g (0.44 mol) acetic anhydride, 1.50 g (0.004 mol) of tetrabutylphosphonium acetate acetic acid complex, and 3.44 g of diglyme (internal standard). The autoclave was purged with helium twice, then the vessel was pressurized to 6.2 bars (75 psig) with helium and agitation started. The reaction mixture was heated to 125° C., then 31.35 mL (0.40 mol) of 3,4-epoxy-1-butene was introduced to the reactor via syringe pump over 10 sec. A first sample was obtained at 1 min, then sequential samples were obtained every 15 min during the course of 105 min for analysis by GC. GC analysis of the crude mixture after 105 min revealed 79% conversion of 3,4-epoxy-1-butene with 98.7% selectivity to 3,4-diacetoxy-1-butene. The reaction was observed to be first order in 3,4-epoxy-1-butene with a first order rate constant of 0.011 min$^{-1}$ (Table 3). This example shows the catalytic effect of tetrabutylphosphonium acetate at high concentration levels of 3,4-epoxy-1-butene relative to acetic anhydride.

EXAMPLE 9

A 100-mL autoclave was charged with 45.25 g (0.44 mol) acetic anhydride, 3.0 g (0.008 mol) of tetrabutylphosphonium acetate acetic acid complex, and 3.44 g of diglyme (internal standard). The autoclave was purged with helium twice, then the vessel was pressurized to 6.2 bars (75 psig) with helium and agitation started. The reaction mixture was heated to 125° C., then 31.35 mL (0.40 mol) of 3,4-epoxy-1-butene was introduced to the reactor via syringe pump over 10 sec. A first sample was obtained at 1 min, then sequential samples were obtained every 15 min during the course of 90 min for analysis by GC. GC analysis of the crude mixture after 90 min revealed 88% conversion of 3,4-epoxy-1-butene with 99.6% selectivity to 3,4-diacetoxy-1-butene. The reaction was observed to be first order in 3,4-epoxy-1-butene with a first order rate constant of 0.017 min$^{-1}$ (Table 3). This example shows the catalytic effect of tetrabutylphosphonium acetate at high concentration levels of 3,4-epoxy-1-butene relative to acetic anhydride.

EXAMPLE 10

A 100-mL autoclave was charged with 45.25 g (0.44 mol) acetic anhydride, 6.0 g (0.016 mol) of tetrabutylphosphonium acetate acetic acid complex, and 3.44 g of diglyme (internal standard). The autoclave was purged with helium twice, then the vessel was pressurized to 6.2 bars (75 psig) with helium and agitation started. The reaction mixture was heated to 125° C., then 31.35 mL (0.40 mol) of 3,4-epoxy-1-butene was introduced to the reactor via syringe pump over 10 sec. A first sample was obtained at 1 min, then sequential samples were obtained every 15 min during the course of 120 min for analysis by GC. GC analysis of the crude mixture after 120 min revealed 99% conversion of 3,4-epoxy-1-butene with 99.8% selectivity to 3,4-diacetoxy-1-butene. The reaction was observed to be first order in 3,4-epoxy-1-butene with a first order rate constant of 0.034 min$^{-1}$ (Table 3). This example shows the catalytic effect of tetrabutylphosphonium acetate at high concentration levels of 3,4-epoxy-1-butene relative to acetic anhydride.

Kinetic Affect of Temperature

Figure 2:
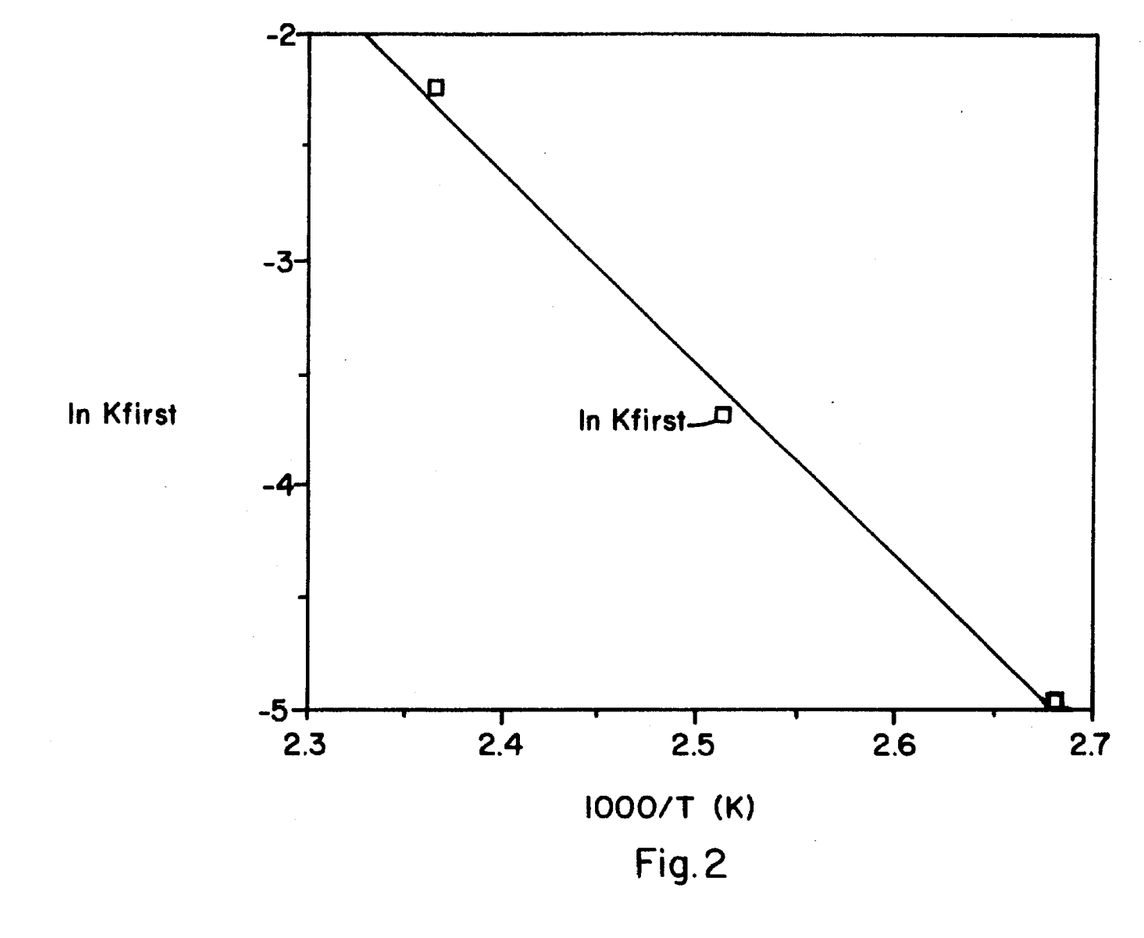
FIG. 2 is a graph demonstrating the affect of temperature on the rate of disappearance of 3,4-epoxy-1-butene in the acetylation of 3,4-epoxy-1-butene with acetic anhydride by the correlation of the ln of the observed first order rate constant versus 1000/T.

The affect of temperature (T) on the rate of addition of acetic anhydride to 3,4-epoxy-1-butene to form 3,4-diacetoxy-1-butene is demonstrated in Examples 11–13 (Table 4). The affect of temperature on the rate of disappearance of 3,4-epoxy-1-butene is used to determine the energy of activation by plotting the ln of the observed first order rate constant versus 1000/T (FIG. 2). The energy of activation is determined by the slope (8.55×1.99) which gives 17.0 Kcal/mole. A linear correlation of 0.995 indicates a very good correlation in the range of 100°–150° C.

TABLE 4

| Example | Temperature (°C.) | Kfirst (min-1) | ln Kfirst | 1000/T (K) |
| --- | --- | --- | --- | --- |
| 11 | 125 | 0.025 | −3.689 | 2.513 |
| 12 | 150 | 0.106 | −2.244 | 2.364 |
| 13 | 100 | 0.007 | −4.962 | 2.681 |

EXAMPLE 11

A 100-mL autoclave was charged with 68.2 mL (0.62 mol) acetic anhydride, 3.75 g (0.010 mol) of tetrabutylphosphonium acetate acetic acid complex, and 3.44 g of diglyme (internal standard). The autoclave was purged with helium twice then the vessel was pressurized to 6.2 bars (75 psig) with helium and agitation started. The reaction mixture was heated to 125° C., then 5.22 mL (0.067 mol) of 3,4-epoxy-1-butene was introduced to the reactor via syringe pump over 5 sec. A first sample was obtained at 1 min, then sequential samples were obtained every 2 min during the course of 14 min for analysis by GC. GC analysis of the crude mixture after 14 min revealed 41% conversion of 3,4-epoxy-1-butene with 98% selectivity to 3,4-diacetoxy-1-butene. The reaction was observed to be first order in 3,4-epoxy-1-butene with a first order rate constant of 0.025 min$^{-1}$ (Table 4). This example shows the temperature dependence on the rate of reaction at 125° C.

EXAMPLE 12

A 100-mL autoclave was charged with 68.2 mL (0.62 mol) acetic anhydride, 3.75 g (0.010 mol) of tetrabutylphosphonium acetate acetic acid complex, and 3.44 g of diglyme (internal standard). The autoclave was purged with helium twice, then the vessel was pressurized to 6.2 bars (75 psig) with helium and agitation started. The reaction mixture was heated to 150° C., then 5.22 mL (0.067 mol) of 3,4-epoxy-1-butene was introduced to the reactor via syringe pump over 5 sec. A first sample was obtained at 1 min, then sequential samples were obtained every 4 min during the course of 28 min for analysis by GC. GC analysis of the Crude mixture after 28 min revealed 95% conversion of 3,4-epoxy-1-butene with 97.8% selectivity to 3,4-diacetoxy-1-butene. The reaction was observed to be first order in 3,4-epoxy-1-butene with a first order rate constant of 0.106 min$^{-1}$ (Table 4). This example shows the temperature dependence on the rate of reaction at 150° C.

EXAMPLE 13

A 100-mL autoclave was charged with 68.2 mi. (0.62 mol) acetic anhydride, 3.75 g (0.010 mol) of tetrabutylphosphonium acetate acetic acid complex, and 3.44 g of diglyme (internal standard). The autoclave was purged with helium twice, then the vessel was pressurized to 6.2 bars (75 psig) with helium and agitation started. The reaction mixture was heated to 100° C., then 5.22 mL (0.067 mol) of 3,4-epoxy-1-butene was introducer to the reactor via syringe pump over 5 sec. A first sample was obtained at 1 min, then sequential samples were obtained every 5 min during the course of 50 min for analysis by GC. GC analysis of the crude mixture after 50 min revealed 21% conversion of 3,4-epoxy-1-butene with 99% selectivity to 3,4-diacetoxy-1-butene. The reaction was observed to be first order in 3,4-epoxy-1-butene with a first order rate constant of 0.007 min$^{-1}$ (Table 4). This example shows the temperature dependence on the rate of reaction at 100° C.

EXAMPLE 14

Figure 3:
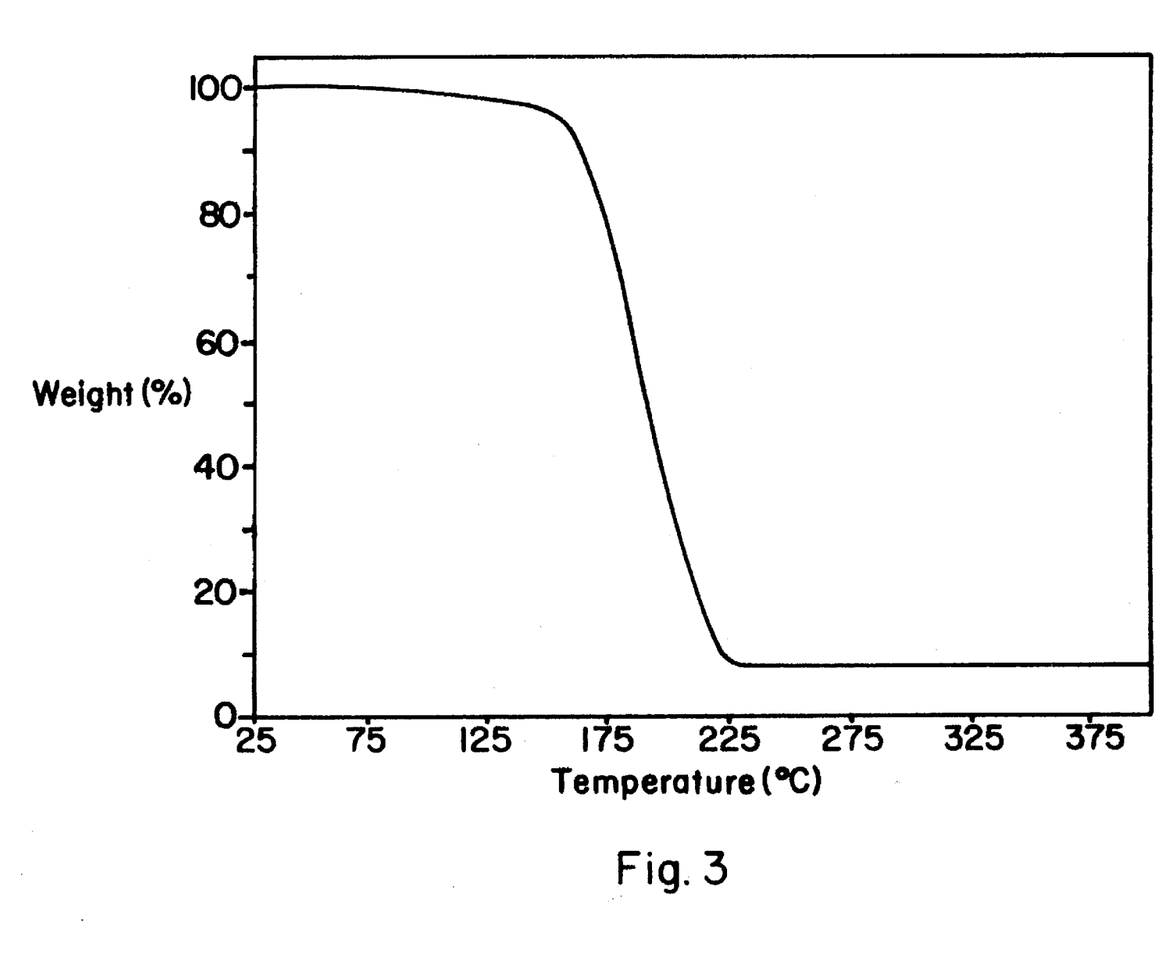
FIG. 3 is a graph of a thermogravimetric analysis on a sample of tetrabutylammonium acetate.
Figure 4:
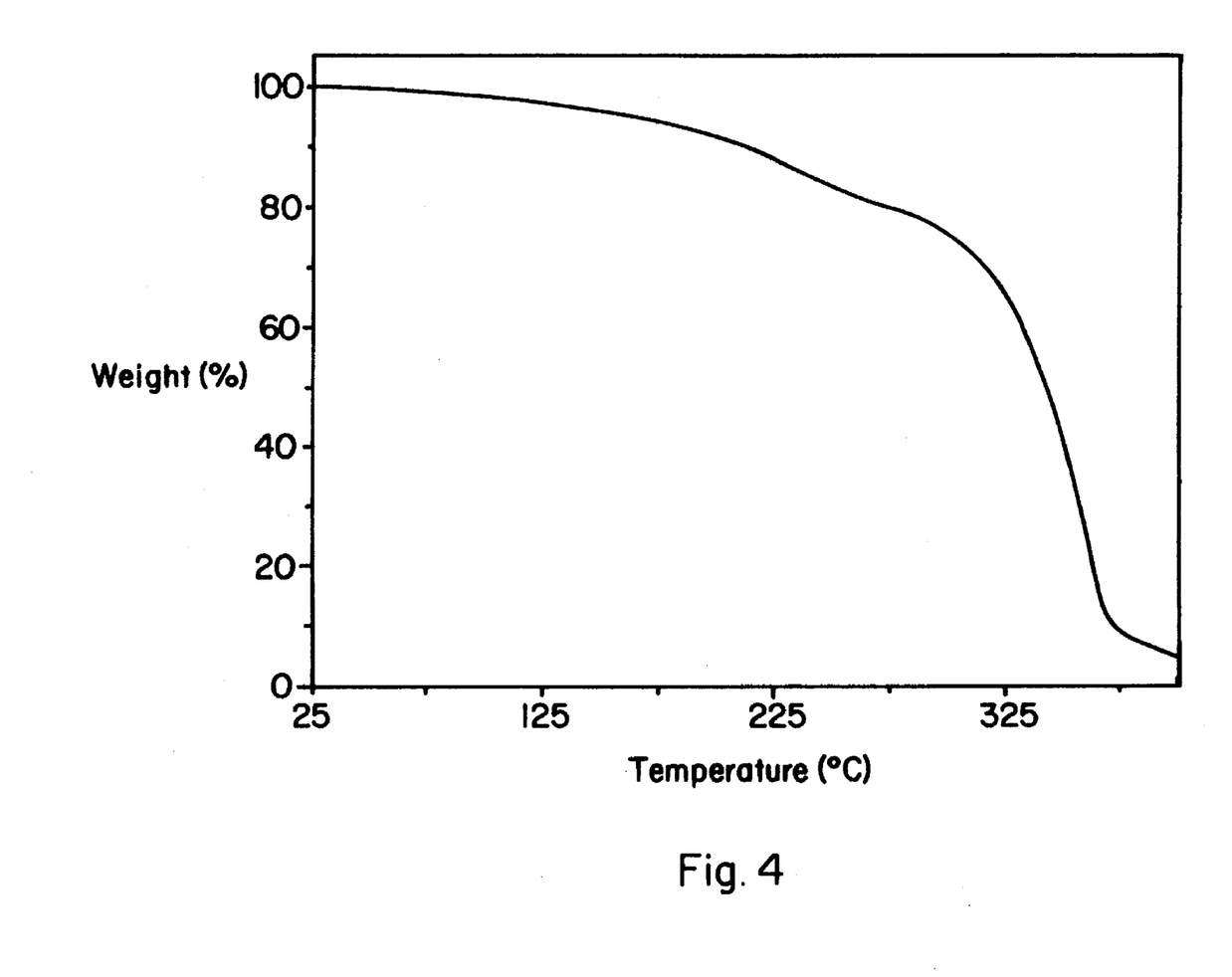
FIG. 4 is a graph of a thermogravimetric analysis on a sample of tetrabutylphosphonium acetate.

The thermal stability of tetrabutylammonium acetate and tetrabutylphosphonium acetate acetic acid complex was evaluated by conducting a thermogravimetric analysis on a sample of their respective salts under nitrogen in the range of 20°–400° C. Tetrabutylammonium acetate rapidly decomposed upon heating over a range of 20°–400° C. at a rate of 40° C./min (FIG. 3). At 165° C., tetrabutylammonium acetate retained 90% of its mass, at 190° C. 50% of its mass and at 230° C. 8% of its mass. Whereas, tetrabutylphosphonium acetate acetic acid complex slowly decomposed upon heating over a range of 20°–400° C. at a rate of 40° C./min (FIG. 4). At 209° C., tetrabutylphosphonium acetate acetic acid complex retained 90% of its mass, at 342° C. 50% of its mass and at 375° C. 10% of its mass. Based on these results the tetrabutylphosphonium acetate acetic acid complex is much more stable than tetrabutylammonium acetate.

Thus, the quaternary phosphonium acetate catalysts or their complexes with acetic acid have now been found to provide an improved catalytic composition for the preparation of 1,2-diacetate esters by the acylation of epoxides with acetic anhydride. The selection of quaternary phosphonium acetates may vary from short to long chain or aromatic phosphonium acetates. The use of catalytic quaternary phosphonium acetates, such as tetrabutylphosphonium acetate, allow the 1,2-diacetate esters to be readily separated because the product may be distilled away from the non-volatile phosphonium salt. Quaternary phosphonium acetates offer an improvement over the prior art use of tetraalkylammonium acetates because they are thermally more stable and may be reused many times.

The invention has been described in detail with particular reference to preferred processes thereof, but it will be understood that variations and modifications can be effected within the spirit and scope of the invention.

What is claimed is:

1. A process for the preparation of a 1,2-diacetoxy ester comprising reacting an epoxide with acetic anhydride in the presence of a quaternary phosphonium acetate catalyst.

2. The process of claim 1 wherein said epoxide contains from 2 to about 20 carbon atoms.

3. The process of claim 1 wherein said epoxide has the formula $(R_2C)_2O$ and contains R substituents independently selected from a group consisting of hydrogen, alkyl or alkenyl of up to about 8 carbon atoms, carbocyclic, aryl or heterocyclic aryl of about 5 to 10 carbon atoms or any two of said R substituents collectively representing alkyl or alkenyl forming a ring.

4. The process of claim 3 wherein said R substituents individually represent hydrogen or a straight or branched chain alkyl or alkenyl of 2 to about 8 carbon atoms.

5. The process of claim 4 wherein two or more of said R substituents represent hydrogen.

6. The process of claim 1 wherein said quaternary phosphonium acetate catalyst has the formula $R'_4P^+$ $^-OAc$ and contains R' substituents independently selected from alkyl, alkenyl or aromatic group of up to 8 carbon atoms.

7. The process of claim 6 wherein said quaternary phosphonium acetate catalyst is selected from the group consisting of tetrabutylphosphonium acetate, ethyltriphenylphosphonium acetate and tetraoctylphosphonium acetate.

8. The process of claim 1 wherein said quaternary phosphonium acetate catalyst is a complex with acetic acid.

9. The process of claim 1 wherein said quaternary phosphonium acetate catalyst is present in an amount ranging from about 0.05 to 50.0 mole percent and said epoxide is present in an amount ranging from about 50.0 to 95.5 mole percent, based on a total amount of said quaternary phosphonium acetate catalyst and said epoxide.

10. The process of claim 9 wherein said quaternary phosphonium acetate catalyst is present in an amount ranging from about 0.1 to 10.0 mole percent and said epoxide is present in an amount ranging from about 99.9 to 90.0 mole percent.

11. A process for the preparation of 3,4-diacetoxy-1-butene which comprises reacting 3,4-epoxy-1-butene with acetic anhydride in the presence of a quaternary phosphonium acetate catalyst.

12. The process of claim 11 wherein said quaternary phosphonium acetate catalyst is a complex with acetic acid.

13. The process of claim 11 wherein said quaternary phosphonium acetate catalyst is tetrabutylphosphonium acetate.

14. The process of claim 13 wherein said tetrabutylphosphonium acetate is a complex with acetic acid.

15. The process of claim 1 wherein said acetic anhydride is reacted in an amount of at least 1 molar equivalent of said acetic anhydride to said epoxide.

* * * * *